United States Patent
Goodsall et al.

(10) Patent No.: US 6,482,450 B1
(45) Date of Patent: Nov. 19, 2002

(54) COLD WATER INFUSING LEAF TEA

(75) Inventors: Christopher William Goodsall; Timothy Graham Jones, both of Bedford (GB); Joseph Kipsiele Mitei, Kericho (KE); Andrew David Parry, Bedford (GB); Richard Safford, Bedford (GB); Ambalavanar Thiru, Bedford (GB)

(73) Assignee: Lipton, division of Conopco, Inc., Englewood Cliffe, NJ (US)

( * ) Notice: Subject to any disclaimer, the term of this patent is extended or adjusted under 35 U.S.C. 154(b) by 0 days.

(21) Appl. No.: 09/498,605

(22) Filed: Feb. 7, 2000

(30) Foreign Application Priority Data

Feb. 8, 1999 (GB) .............................................. 9902777

(51) Int. Cl.[7] .............................. A23F 3/08; A23F 3/12; A23F 3/14; A23L 1/272
(52) U.S. Cl. .......................... 426/52; 426/262; 426/597
(58) Field of Search ........................... 426/597, 52, 262

(56) References Cited

U.S. PATENT DOCUMENTS

| | | | |
|---|---|---|---|
| 3,812,266 A | 5/1974 | Sanderson et al. |
| 3,903,306 A | 9/1975 | Fairley et al. |
| 4,051,264 A | 9/1977 | Sanderson et al. |
| 5,879,730 A | * | 3/1999 | Bouwens et al. |

FOREIGN PATENT DOCUMENTS

EP      0 760 213 A1    3/1997

OTHER PUBLICATIONS

International Search Report (PCT/GB 00/000359).

* cited by examiner

*Primary Examiner*—Anthony J. Weier
(74) *Attorney, Agent, or Firm*—Edward A. Squillante, Jr.

(57) ABSTRACT

A method for preparing a cold water infusing leaf tea. Green tea leaves are macerated, treated with tannase, fermented in the presence of hydrogen peroxide in an amount that is sufficient to activate endogenous peroxidases to oxidise gallic acid and other compounds that are liberated by the tannase treatment, and then dried. The final product is a black leaf tea that infuses in hot or cold water to give good flavour and colour.

13 Claims, 7 Drawing Sheets

COLD WATER INFUSING LEAF TEA

The present invention relates to a method for manufacturing cold water infusing leaf tea. The method involves fermenting tannase pre-treated dhool (macerated tea leaves) under solid-state conditions in the presence of hydrogen peroxide. The dried leaf product infuses in cold water to give good flavour and colour.

BACKGROUND AND PRIOR ART

Black leaf tea is traditionally produced by oxidising and drying freshly plucked green tea leaves. Tea, the beverage, is generally prepared in Commonwealth countries by brewing these tea leaves in freshly boiled water for a few minutes and adding milk, and perhaps a little sugar. However in some countries, notably the United States (or more accurately, parts thereof) tea is more commonly enjoyed as an iced beverage.

Such a beverage cannot be prepared conveniently by infusing traditionally manufactured tea leaves in cold water. Instead, Americans either infuse the leaves in hot water, remove the leaves and place the infusion in a refrigerator until it is ready to consume or place tea leaves in cold water in sunlight to infuse slowly over a period of hours.

The numerous compounds in the leaves that give the beverage its unique organoleptical properties are only sparingly soluble in cold water. A more convenient option that has become available in the 1970's is the use of cold soluble tea-based powders.

There are numerous methods for making cold water soluble tea powders.

U.S. Pat. No. 4,051,264 (Lipton/Sanderson) discloses a method for making a cold water soluble leaf tea extract. Tea leaves are pre-treated with tannase under anaerobic conditions to generate a cold-water infusing tea with good colour, yield and flavour.

U.S. Pat. No. 3,812,266 (Sanderson/Coggon) discloses a method that involves converting green tea to black using tannase and natural tea enzymes. The method also includes a tannase pre-treatment step, but in a slurry system, followed by oxidation by natural tea enzymes to convert green tea into black, and generate tea powders, which are both hot and cold water soluble. In some examples hydrogen peroxide is added, to "shorten the process". The proposed mechanism for enhanced cold-water soluble colour generation resulting from tannase-treatment (elevated epitheaflavic acid levels) is now known to be incorrect, and no mechanism was presented to explain the effect of adding the hydrogen peroxide.

European patent specification EP 760,213 A1 (Unilever) discloses a method of enhancing colour in a tea-based foodstuff. The method involves using a tannase pre-treatment (on leaf or extract) followed by treatment with exogenous peroxidase and hydrogen peroxide to generate cold-soluble colour.

International patent publication WO 97/40699 (Unilever) concerns tea processing with zeolites to generate colour. There are examples of adding zeolite following tannase treatment to generate cold-water soluble tea.

U.S. Pat. No. 4,639,375 (P&G, Tsai) discloses treating black tea with tannase, together with other cell-wall digesting enzymes, to generate cold-water soluble instant tea powders.

Convenient as cold water soluble tea powders can be, for many consumers the quality of the final beverage is not equal to that prepared from hot infused leaves. Other consumers prefer not to use powders as they perceive them to be artificial and therefore "unnatural".

The present inventors have surprisingly found that it is possible to make a leaf tea that infuses in cold water to give a beverage with good colour and flavour that is as acceptable to consumers as a hot infused black leaf tea that has been refrigerated. Furthermore this product can be made by modifying the traditional black tea manufacturing process.

STATEMENT OF THE INVENTION

In broad terms the present invention relates to a method for preparing a cold water infusing leaf tea comprising the steps of macerating green tea leaves, treating the macerated leaves with tannase, fermenting the tannase-treated macerate in the presence of an amount of hydrogen peroxide that is sufficient to activate endogenous peroxidases, and drying the fermented leaf material to yield the cold water infusible leaf tea.

The invention also relates to a method for generating colour species in a cold water soluble tea product comprising adding hydrogen peroxide to a tannase-treated macerate of green tea in a quantity that is sufficient for the endogenous peroxidases to oxidise gallic acid liberated by the tannase treatment.

"Tea" for the purposes of the present invention means leaf material from *Camellia sinensis* var. *sinensis* or *Camellia sinensis* var. *assamica*. It also includes rooibos tea obtained from *Aspalathus linearis* however that is a poor source of endogenous fermenting enzymes. "Tea" is also intended to include the product of blending two or more of any of these teas.

"Leaf tea" for the purposes of this invention means a tea product that contains one or more tea origins in an uninfused form.

"Cold water soluble" for the purposes of this invention means giving good colour, flavour and mouthfeel in a short infusion time i.e. less than 10 minutes, but preferably less than 5 minutes at a temperature at or above 4° C.

The macerated leaves are preferably tannase treated under anaerobic conditions. The process is effective without this anaerobic incubation provided sufficient tannase is used. The tannase treated macerate is preferably fermented under standard conditions to produce elevated levels of theaflavins and gallic acid prior to the addition of hydrogen peroxide.

For the avoidance of doubt the word "comprising" is intended to mean including but not necessarily "consisting of" or "composed of". In other words the listed steps or options need not be exhaustive.

DETAILED DESCRIPTION OF THE INVENTION

Tea manufacture, especially black tea manufacture, traditionally comprises four basic steps: withering, rolling, fermenting and firing.

Withering is a process whereby the plucked tea leaves are stored for periods of time (perhaps up to 24 hours), during which they undergo various biochemical and physical changes which often includes a loss of moisture.

Maceration follows the withering step, and traditionally the withered leaves are optionally rolled to bruise and crush the leaves i.e. break down the plant tissue structure. This will have the effect of liberating fermentable substrates and fermenting enzymes from within the plant cells and tissue. Modern tea manufacture usually includes this step however the plant cells and tissue is broken down by passing tea, which has usually been withered, through a cutting machine.

The next step is commonly called fermentation but that is a misnomer. "Fermentation" is commonly used in the context of brewing alcohol to describe the action of exogenous enzymes. However in the tea world it is used to refer to the oxidative process that tea undergoes when certain endogenous enzymes and substrates are brought together by mechanical disruption of the cells by tearing or cutting the leaves. During this process colourless catechins in the leaves are converted to a complex mixture of yellow and orange to dark-brown substances and producing a large number of aromatic volatile compounds.

The colourful oxidation products include theaflavins and thearubigens. Theaflavins comprise several well-defined catechin condensation products that are characterised by their benzotropolone ring. Thearubigens are a group of undefined molecules with a large variance in molecular weight. They have a large variety of colours ranging from yellow to dark red and brown.

The fermented product is fired and dried to give a black leaf tea. The firing involves heating and drying the tea to destroy the fermenting enzymes and thereby arrest fermentation. It results in a reduction of moisture content to below 5%, and also leads to further chemical oxidation and changes in tea aroma. This generally involves exposing the tea to a blast of hot, dry air in a dryer.

The present invention relates to method for making cold soluble black leaf tea. The present inventors have found that this can be achieved by modifying some of the steps of the traditional tea manufacturing process just described.

Figure 1:
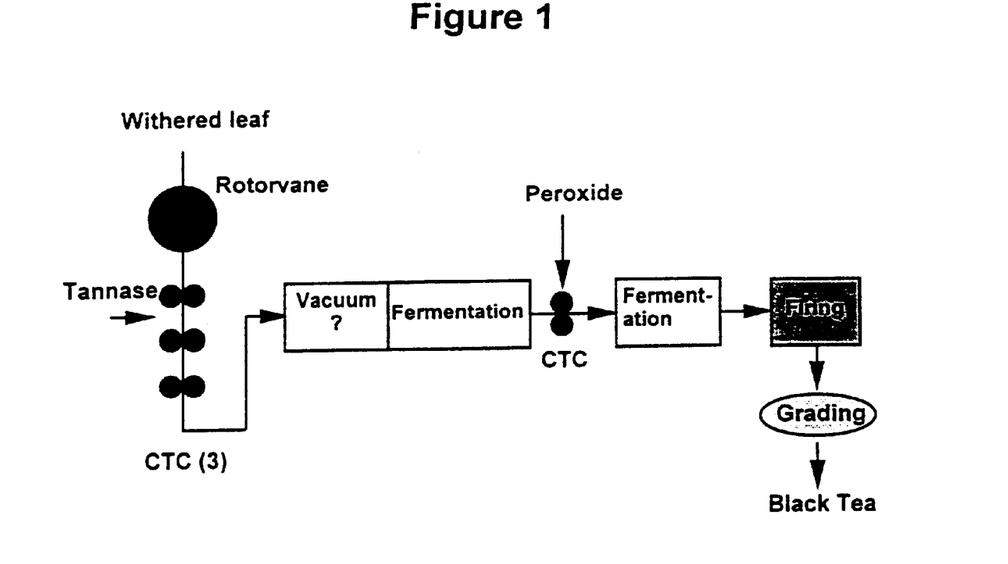
FIG. 1 is a diagram that shows a preferred process layout of the invention.

A preferred embodiment of the method of the invention is depicted in FIG. 1. In that preferred embodiment freshly plucked green tea leaves are withered in the normal way using any of the art known techniques. Withering is not essential to the invention but it can be a useful means to enhance tea aroma and also to reduce initial moisture content (which is important as moisture will be added with the tannase and peroxide, and drying efficiency can be affected at high moisture contents i.e. greater than 76%).

The leaves are macerated, which could mean being comminuted by a rotorvane and/or by a number of CTC (cut-tear-curl) machines.

In a first departure from traditional black tea manufacture the macerated leaves are treated with tannase (flavanol gallate esterase) to generate degallated catechins and gallic acid. This subsequently leads to the generation of theaflavins and non-gallated thearubigens during fermentation (which are more soluble than the gallated ones).

The general reaction catalysed by tannase is the cleavage of gallate ester linkages, both on gallated catechins and also from other gallated compounds within the leaf. Tannase is also well known to improve the clarity of tea products since galloyl groups are important in cream formation and tannase has been used extensively for the degallation and solubilisation of black tea cream.

Tannase is known to be useful for treating green tea prior to slurry fermentation. For example the aforementioned U.S. Pat. No. 3,812,266 (Sanderson et al) discloses using tannase to reduce the amount of tea cream in liquors. Improved colours generated by the process were also noted.

The present invention however does not require the tea to be suspended and fermented in a slurry. Indeed this would be counter-productive because the components necessary to give good colour and flavour from the leaf would be prematurely extracted into the slurry. Rather the tea is fermented under solid-state conditions. This is an important distinction. The inventors previously thought that extraction of the catechins into a slurry liquor was essential for efficient action of tannase. They were surprised that direct application of tannase to the dhool in a solid-state led to efficient (i.e. almost complete) catechin degallation and high levels of theaflavin generation. They were even more surprised that the leaf product infused in cold water.

Tannase treatment degallates the gallated catechins ECG and EGCG to produce the degallated catechins EC and EGC. On subsequent oxidation during fermentation the catechins EC and EGC react to produce theaflavin.

The tannase can be applied using a variety of art-known techniques. The present inventors prefer to dissolve tannase in water, spray the solution onto the dhool and leave the mixture to react for a suitable time at a suitable temperature. The tannase is applied to the dhool after an initial maceration (for example, a first CTC cut) in a fine spray followed by subsequent cutting (for example, a second or third CTC cut) to ensure adequate mixing. The dhool is preferably incubated under vacuum, or under anaerobic conditions for example in an atmosphere or nitrogen. This prevents fermentation occurring. It is preferable that complete degallation takes place before fermentation starts as this results in maximal theaflavin levels in the subsequent fermentation, which in turn leads to optimal colour generation.

The present inventors postulated that one might increase the efficiency by which certain exogenous compounds can access certain endogenous compounds of solid state tea by using a vacuum to draw the exogenous molecules into the macerated tea leaves and into contact with the compounds therein. Vacuum infiltration per se is known. However it has been used to force substances between cells rather than into cells. And those substances have tended to have small molecular weights.

The present inventors have however developed a method for bringing certain exogenous compounds into contact with endogenous compounds found in tea that involves vacuum infiltrating macerated tea leaves with those exogenous compounds and applied it to modify certain properties of tea and tea based beverages. The extent to which this method allows even large molecules such as enzymes to access endogenous tea compounds and modify certain properties of tea has been truly surprising. For example, an infusion of tannase pre-treated tea has been found to have more than double the total theaflavin content of a control and a six fold increase in TF1.

Vacuum infiltration is a technique that is often used in the preparation of protoplasts from plant tissue, albeit to introduce substances between rather than into cell walls. Cut leaf tissue is incubated in a solution containing tannase. The suspension is then placed under vacuum and air is drawn from the intracellular spaces of the leaf particles, the enzyme solution is drawn in to replace it. The inventors have found that a vacuum less than 100 mbar is suitable for this.

The major constraint when applying this method to tea dhool is achieving access within the cells. Another major problem is that large volumes of water can seriously affect the quality of tea, by reducing oxygen uptake during fermentation. The results described in the Examples indicate that vacuum infiltration is a useful tool for introducing enzymes, for example tannase, into solid state dhool. When fermented, tannase treated dhool gives rise to black tea with high levels of theaflavin and no gallated species. This enables one to produce a range of novel teas. Vacuum assisted tannase treatment is much more effecgive in removing gallated species and enhacing additional TF formation than the equivalent treatment under ambient temperature and pressure. The vacuum allows the enzyme to penetrate the tissue and remove gallated species prior to fermentation, they key feature of tannase driven theaflavin enhancement, compared to simply applying the enzyme onto fermenting dhool and mixing in by hand.

If at all possible the conditions should be adjusted to prevent any fermentation prior to or during tannase treatment. This can be achieved by using a stronger vacuum pump, holding the dhool under $N_2$ sparge, or shortening the tannase treatment.

Tannase can be applied to the macerated tea by a simple dosing. However, spraying the tannase in a fine mist is preferably as it aids infiltration.

Suitable conditions can be readily determined by experiment. Good results have been obtained with KIKKOMAN's tannase (KIKKOMAN is a trade mark of Kikkoman Corporation, Tokyo, Japan) in an amount of 1–100 mg/kg dhool, preferably 10–80 mg/kg dhool but more preferably 40–80 mg/kg dhool. Note: KIKKOMAN's tannase has 50,000 tannase activity units/gram.

Fermentation is preferably carried out at a pH in the range of 4.0 to 5.5. The fermentation temperature is preferably in the range 15 to 40° C. Fermentation is preferably carried out for a time in the range 30 to 150 minutes, more preferably 105 to 120 minutes. However in a second departure from traditional black tea manufacture hydrogen peroxide is added, after a time that is sufficient to generate gallic acid and theaflavin during the fermentation step, to activate (or at least greatly enhance the activity of) endogenous peroxidase.

Tea is known to contain natural peroxidase at high levels. It is also known that natural peroxidase can be activated (or have its activity enhanced) through the addition of hydrogen peroxide in a slurry system. J. Sci. Food Agric. vol. 32, p 920–932 (Dix., 1981) discloses such a system and process. The article mentions that peroxidase can oxidase tea polyphenols to form theaflavins and also thearubigens which may be similar and different to those produced under "normal" fermentations. However it does not offer any detailed understanding as to the chemistry at work.

Figure 2:
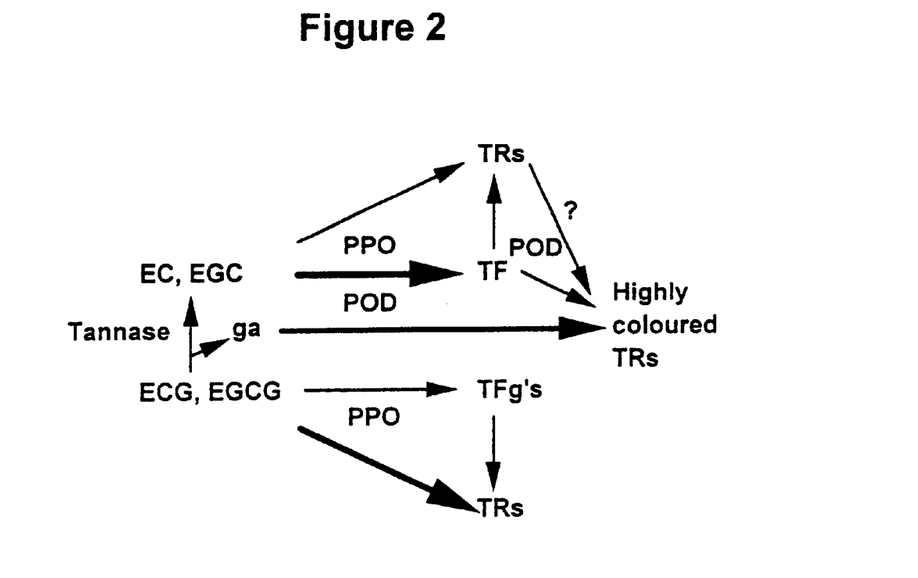
FIG. 2 is a diagram that represents that chemical reactions that tannase and endogenous peroxidase catalyse to give highly coloured thearubigens.

The present inventors have found that the endogenous peroxidases have the potential to oxidise catechins to theaflavins and thearubigens, convert theaflavins to thearubigens and, unlike endogenous polyphenol oxidase, readily oxidise gallic acid. The combination of these reactions generates significant amounts of coloured compounds that are soluble in cold water. The chemistry involved here is represented in FIG. 2.

The hydrogen peroxide is added in an amount that is sufficient to activate endogenous peroxidases and oxidise gallic acid liberated by the tannase treatment. One skilled in the art can determine that by experiment. However the present inventors prefer to use between 100 and 200 ml of 2.0 to 2.5% hydrogen peroxide per kg dhool, but preferably 160 ml of 2.0% hydrogen peroxide per kg dhool. Under normal conditions of tea manufacture peroxidase is largely inactive, due to the low endogenous levels of hydrogen peroxide and high activities of catalase. Measurements have shown that all added hydrogen peroxide is consumed during the process, with none remaining in the final made tea. In contrast to the findings disclosed in the aforementioned U.S. Pat. No. 4,051,264 the present inventors have found that the combination of tannase treatment and subsequent activation of peroxide is critical for the manufacture of a product that gives good colour and acceptable taste. Product that was only tannase treated had a "sour" or "metallic" note.

As one would expect, the colour and taste profile of a beverage made from the cold water infusing leaf tea of the present invention depends to a large extent on the source and quality of the raw material i.e. tea leaves. The present inventors have found that standard raw material, two leaves and a bud delivered to the factory within excess of 1100 shoots per kilogram green leaf tea, can be processed according to the method of the invention to give very good colour and taste. However during efforts to improve the colour and taste even further the inventors surprisingly found significant improvement to both can be achieved by using more mature leaf.

Tea is generally harvested as two leaves and a bud on a 17 day cycle to optimise quality and yield. Extending the cycle means the leaves will be more mature and their chemical composition will be a little different. One then needs to pluck larger portions of tea plant to account for the extra growth. Such a harvesting strategy increases the yield per hectare of tea and thus improves productivity but the harvested plant material tends to have longer stems and a higher stem to leaf ratio.

Black tea made from mature tea leaf material tends to be less coloured and thinner after infusion than black tea made from tea portions of two leaves and a bud that are harvested on a 17 day cycle. However, the present inventors surprisingly found that when mature leaf tea, i.e. tea leaves harvested on a 30 to 50 day cycle in portions of 3 to 5, but preferably 4 leaves and a bud, is used there is a significant increase in cold water infusion performance and thus an improvement in colour and taste.

While not wanting to be bound by theory, it is thought that mature leaf material (including stalk) contains higher levels of peroxidase than standard leaf and this peroxidase provides an important role in the maturation cascade. This means more peroxidase is available when hydrogen peroxide is added when carrying out the method of the invention. Consequently more colour is generated by an enhanced peroxide/peroxidase oxidation system.

The method of the invention will now be described with reference to the following examples and the accompanying drawings.

In the drawings:

FIGS. 5 and 6 represent the fermentation profiles for the experiments described in Example 4a.

EXAMPLE 1

Lab Scale Process (a) Process Steps 60 mg tannase dissolved in 24 ml water was sprayed onto 100 g of frozen dhool. The dhool was then thawed under $N_2$ and once it had reached 20° C. it was placed under vacuum (50 mbar) for 60 minutes. The dhool was then fermented for 60 minutes at 25° C., 100% RH. After fermentation the dhool was sprayed with 12.5 ml ~2% hydrogen peroxide solution, placed under vacuum for 15 minutes and then dried by a fluid bed drier (conventional FBD). One can increase the level of theaflavins by pre-treating the dhool with tannase. Peroxide is added to activate the endogenous tea peroxidase. This enzyme oxidises theaflavins and the gallic acid released by tannase to give dark, cold water soluble pigments.

Figure 3:
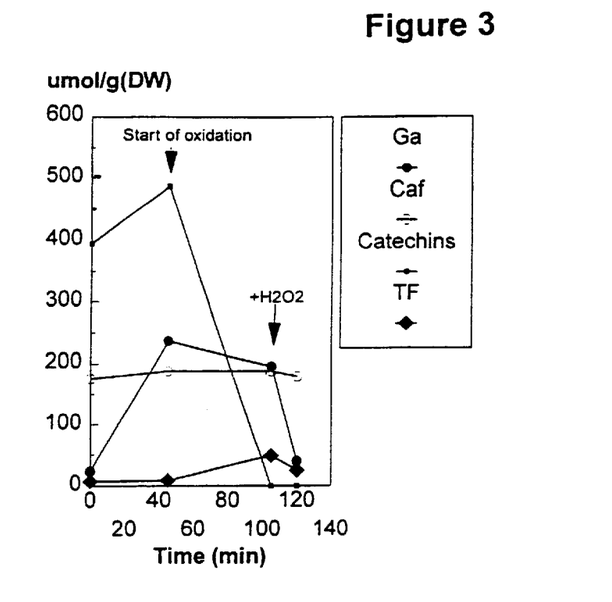
FIG. 3 is a formulation profile of tannase—peroxide treated partially fermented dhool (Example 1).

The fermentation profile is represented in FIG. 3.

(b) Taste Testing

A cold water infusion made from tea prepared by the process just described was taste tested by an experienced tea taster. The infusion was made in 200 ml of carbon filtered water for 5 minutes at 15° C. The treated sample was described as having a "fruity note, good mouthfeel, astringent, lots of body, low aromatics, good colour, good ice tea product, stands up to ice" whilst the control, standard black tea, was described as "bland". The results of colour, haze and solids analyses are given in Table 1 below where $L^*$ is a measure of luminosity and $a^*$ is a measure of red/green colour as determined using a MINOLTA™ calorimeter.

TABLE 1

Lab scale process product

|  | $L^*$ | $a^*$ | Haze | Solids |
|---|---|---|---|---|
| Control | 54.6 | 23.6 | 26.8 | 0.2 |
| Treated tea | 29.2 | 34.6 | 29.4 | 0.24 |

EXAMPLE 2

Colour Comparison with Other Products

Dhool was treated in treated in accordance with the basic lab scale process described above (60 mg tannase, dried immediately after peroxide addition). The colour of the liquor obtained from this product was compared with that obtained from a commercially available product (SMOOTHBLEND™) and a tea sample prepared from a standard fermentation of Kenyan tea leaf, all at 2.27 g black tea/200 ml chilled tap water, 5 minutes infusion. The results are summarised in Table 2 below. Note, these values are for tap water infusions which gives darker colours than infusions in distilled water.

TABLE 2

Colour comparisons with other products

|  | $L^*$ | $a^*$ | $b^*$ |
|---|---|---|---|
| Tannase/peroxide | 59.43 | 12.54 | 57.09 |
| SMOOTHBLEND (TM) | 94.22 | −2.09 | 16.22 |
| Kenyan | 80.16 | 3.67 | 41.14 |

These results show the tannase/peroxide process on the invention gave a liquor whose colour was significantly brighter, redder and yellower than that obtained from the untreated Kenyan tea or the SMOOTHBLEND™ product.

EXAMPLE 3

Figure 4:
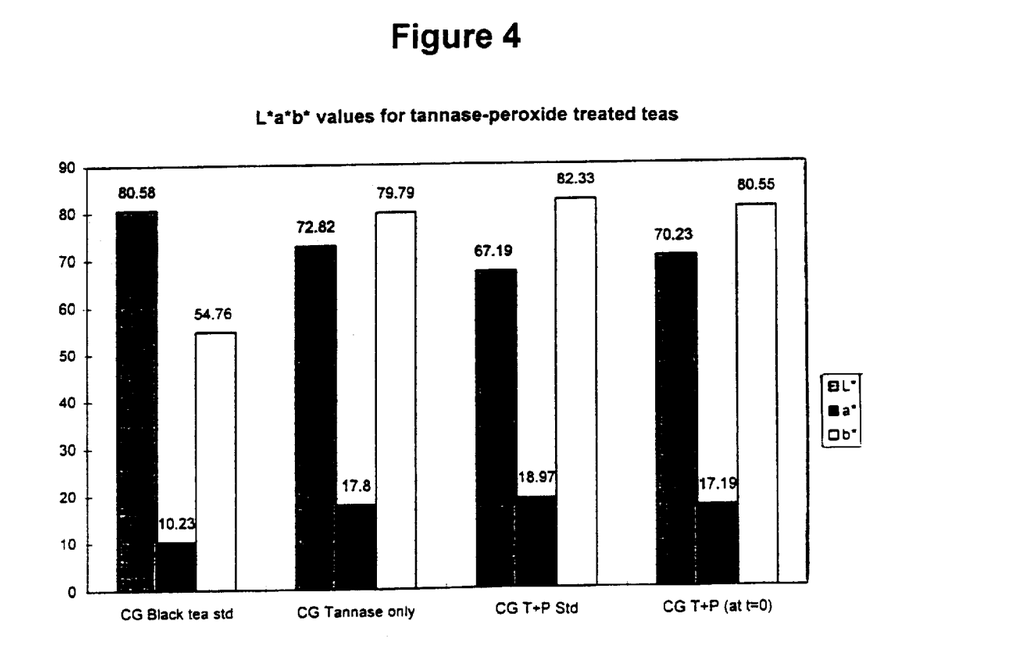
FIG. 4 is a histogram comparing the colour characteristics of tannase-peroxide treated and untreated tea infusions (Example 3).

Comparison of Standard, Tannase Only, Tannase Peroxide (Different Times of Addition) Processes Infusions were made for samples of a black tea standard, tannase treated black tea, tannase-peroxide treated black tea wherein the peroxide was added after 60 minutes fermentation, and tannase-peroxide treated black tea wherein the peroxide was added at t=0. In each case 2.27 g tea was brewed for 5 minutes in 200 ml HIGHLAND SPRING™ still spring water at room temperature. The colour characteristics of each were measured using a MINOLTA transmission calorimeter. The results are represented in FIG. 4.

These results and product tastings demonstrate that the combination of tannase treatment and hydrogen peroxide addition, after partial fermentation, are required to maximise the delivery of colour and flavour. Tannase only samples were observed to possess a "sour" or "metallic" taste thought to be derived from the elevated levels of gallic acid.

The lab scale process described above was repeated and in addition comparison was made with an experiment where tannase was not added, but in its place an amount of gallic acid equal to that released by tannase was added prior to hydrogen peroxide addition. The colour of the liquors obtained from the treated products were measured using a MINOLTA™ calorimeter. The results are given in Table 3 below where L*, is a measure of luminosity, a* is a measure of red/green colour, and b* is a measure of yellow/blue colour.

TABLE 3

Lab scale process variations

| | Treatment | | |
|---|---|---|---|
| | controlled/infusion in distilled water | 60 mg tannase + vacuum | Gallic acid – tannase |
| Infusion conditions | 2.27 g/200 ml. 5 min, 15° C. | | |
| L* | 90.33 | 84.65 | 91.63 |
| a* | −1.33 | 2.27 | −4.99 |
| b* | 47.36 | 80.43 | 52.57 |

This experiment shows that addition of gallic acid alone is insufficient to generate cold-infusing colour/flavour.

EXAMPLE 4

Investigation of the Use of a Vacuum to Optimise Tannase Effectiveness

The experiments that are described below were carried out using some standardised materials and methods. For completeness these are as follows:

Materials

Experiments were carried out with Kenyan leaf of BBK (Brooke Bond Kenya) clone 35, withered overnight at Mabroukie factory and air-freighted to the UK frozen on dry ice. This leaf was stored frozen at −80° C. until use. Tannase was from Kikkoman's Co, Japan and "Macer8 W"™ from Biocatalysts Ltd, Wales.

Tannase Treatment

Batches of dhool were prepared from frozen leaf of BBK 35 and stored at −80° C. Portions of the batch were analysed for initial catechin composition and the remainder used in experiments. Experiments were carried out with various amounts of dhool; 8 g (for the standard experiment) to 100 g (for the scale up experiment). When more than 8 g was used the volume of tannase solution was scaled up appropriately.

Eight grams of dhool were thawed to room temperature under a stream of $N_2$.

After tannase treatment some samples were fermented at 25° C., 100% RH, for up to 2 hours in a TEACRAFT™ controlled environment chamber. Tea was dried in a TEACRAFT™ fluid bed dryer at 120° C. air inlet temperature for 5 minutes then at 90° C., for 20 minutes. At appropriate times portions of the dhool were taken and immediately frozen in liquid nitrogen and stored at −80° C. until analysed.

In a variation upon this, a solution (1–2 ml) containing around 5 mg tannase (see results) was then pipetted onto the dhool, trying to achieve an even spread. The flask was attached to a vacuum line for 45 to 60 minutes. Initially a bench top vacuum tap was used but in later experiments an EDWARDS™ vacuum pump was used as this provided a stronger vacuum.

Analysis of Polyphenols

One gram of dhool was refluxed for 30 minutes in 40 ml 70% (v/v) aqueous methanol. After cooling, the extracts were deleafed by filtering through 50 mm nylon mesh and their volume determined. A 200 μl aliquot was then added to 800 μl antioxidant solvent and then analysed by reverse phase HPLC using diode array detection.

Dry Weight Measurement

The dry weight of dhool samples were determined by mass difference following drying at 100° C. overnight. Results are expressed on a dry weight basis because moisture changes during $N_2$ sparge, and following tannase addition make a fresh weight basis unreliable.

Preparation of Tea Infusions

Infusions were prepared at 1% (w/v) tea solids, 5 minutes infusion time.

EXAMPLE 4a

Effectiveness of Tannase Against Solid State Dhool

In the first experiment, after thawing under $N_2$, 8 g dhool was held under vacuum (using bench top vacuum tape) and 1 ml tannase solution was pipetted on to the dhool (5 mg/ml tannase, 31.25 μg (dhool)) and left for 60 minutes. Catechin composition was determined before and after this treatment. The results are given in Table 4 below:

TABLE 4

Effect of tannase addition under Vacuum on catechin composition of BBK35 dhool

| | | μmol/g (DW) | | | | | | |
|---|---|---|---|---|---|---|---|---|
| | % Moisture | G. acid | Caffeine | EGC | EC | EGCG | ECG | TF |
| T = 0 | 70.8 | 27 | 150 | 224 | 67 | 153 | 51 | 0 |
| T = 60 | 77.4 | 227 | 137 | 303 | 107 | 5 | 0 | 13 |
| Change | +6.6 | +200 | −13 | +79 | +40 | −148 | −51 | +13 |

Degallation was almost entirely complete with only 5 μmol/g (DW) residual EGCG after 60 minutes. The decrease in EGCG and ECG (total—198 μmol/g (DW) was exactly mirrored by the increase in gallic acid (+200 μmol/g (DW)). However there was also evidence that some fermentation had taken place during the process; 13 μmol/g (DW) TF had formed and the increases in EGC and EC were not as high as predicted from the decreases in EGCG and EC were not as high as predicted from the decreases in EGCG and ECG. There were no gallated theaflavins present. The increase in TF accounts for the missing EC/ECG but not the ECG/EGCG which suggests that some thearubigins were formed as well. These results indicate that some fermentation was occurring during the tannase treatment and that perhaps small amounts of gallated theaflavins were being formed and then degallated. Although it was surprising that there was a degree of fermentation under vacuum, it may be that the vacuum was not sufficiently strong to prevent it or that the apparatus used was not absolutely air tight. Nonetheless this proves that vacuum infiltration of tannase is very effective in degallating gallated catechins.

In the next experiment, the process was scaled up so that samples could be taken during the fermentation (to follow the profile of catechin oxidation) in solid state dhool following tannase treatment. Dhool (25 g) was thawed under $N_2$ and treated with 15 mg tannase dissolved in 6 ml water and then held under vacuum for 60 minutes. At the end of this treatment the dhool was transferred to a controlled environment cabinet and fermented at 25° C., 100% RH (relative humidity), for 2 hours. Samples were taken at 30 minute intervals to follow the fermentation profile. The results are given in Table 5 below.

Figure 6:
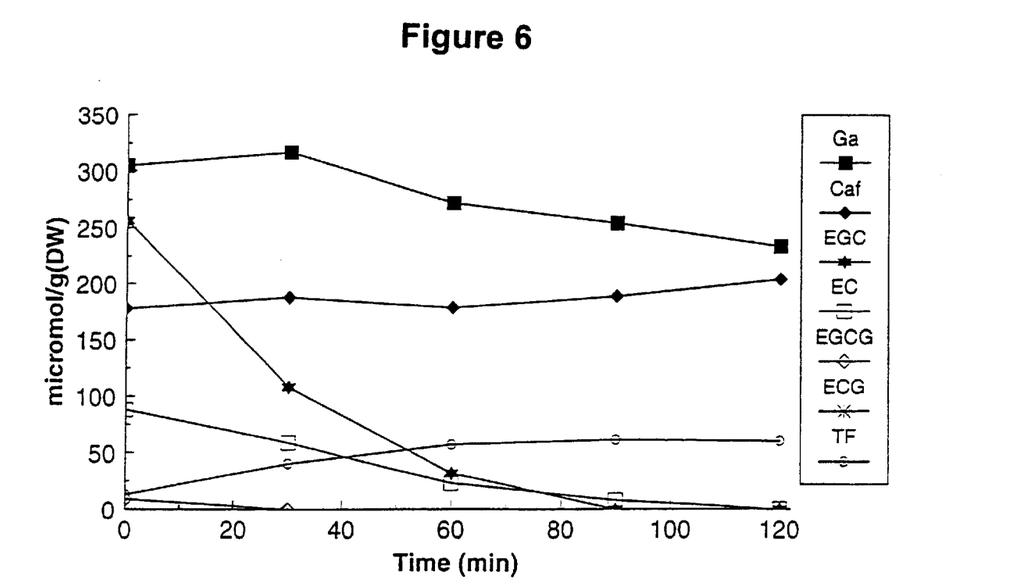

The enhancement in theaflavin following tannase pretreated fermentation of solid state dhool, is compared to a standard tea prepared from the same batch of dhool in FIG. 6 (see the drawings).

In any case these experiments demonstrate the vacuum infiltration enhances the ability of tannase to degallate catechin gallates and provides a raw material suitable for the formation of high levels of theaflavin during fermentation. However, some fermentation is occurring during the tannase treatment.

EXAMPLE 4b

Preparation of Black Tea with Enhanced Theaflavin Level

Having produced fermented dhool with enhanced theaflavin levels the next stage was to use this method to produce a tannase treated black tea so that the properties of the infusion could be assessed. The process was further scaled

TABLE 5

Changes in catechins during Tannase treatment prior to fermentation

| | | | μmol/g (DW) | | | | |
|---|---|---|---|---|---|---|---|
| % Moisture | G. acid | Caffeine | EGC | EC | EGCG | ECG | TF |
| t = 0  75.2 | 32 | 195 | 174 | 47 | 217 | 82 | 0 |
| t = 60  78.3 | 305 | 178 | 256 | 88 | 9 | 0 | 13 |
| change  +3.1 | +273 | −17 | +82 | +41 | −206 | −82 | +13 |
| $t_{60}-t_0$ | | | | | | | |

Once again degallation was almost complete with on 9 μmols of EGCG remaining after 60 minutes in tannase treatment.

Figure 5:
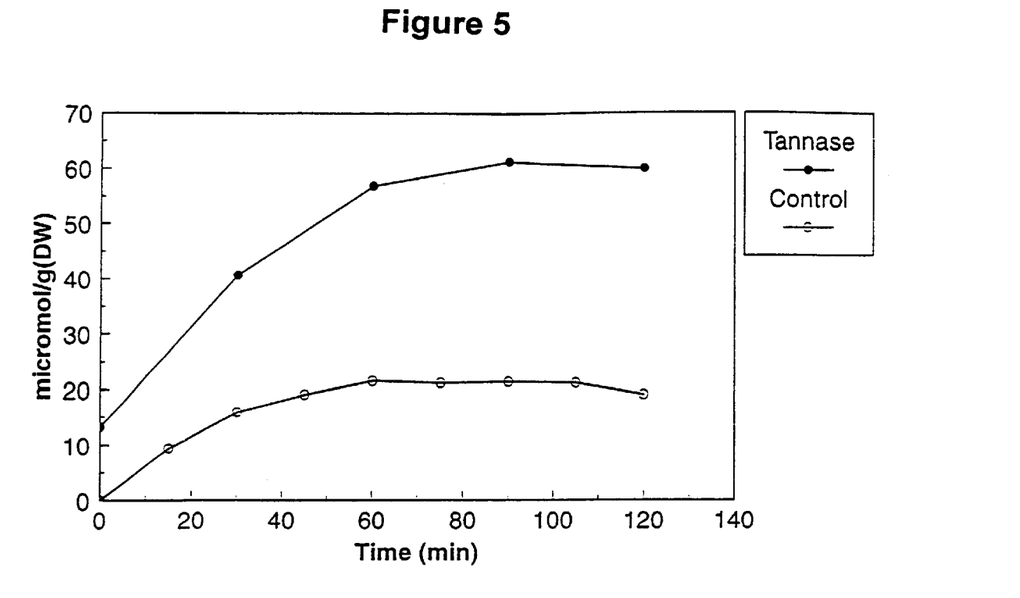

It would seem the increase in gallic acid accounted for the combined decrease in EGCG/ECG. However the increases in EGC and EC did not account for decreases in EGCG and ECG, which indicated that again some fermentation had taken place during the tannase treatment and indeed some theaflavin had formed. The fermentation profile for this experiment is shown in FIG. 5 (see the drawings). EGC and EC were completely oxidised by 90 minutes, and theaflavin levels peak at over 60 μmol/g DW (ie dry weight).

up to 100 g of dhool so that the material could be fluid bed dried after fermentation. The dhool (100 g) was thawed under $N_2$ and 24 ml $H_2O$ containing 60 mg tannase added. The dhool was then placed under vacuum, using an EDWARDS™ vacuum pump for 60 minutes. After this time the dhool was placed in a controlled environment chamber and fermented at 25° C., 100% RH for 120 minutes. After this the dhool was fluid bed dried. A replicate batch of tea was also prepared but without any tannase addition. Catechin levels before and after tannase treatment and after fermentation are shown in Table 6 below.

TABLE 6

Catechin and theaflavin Composition of tannase and control teas

| | | | | Mmol/g (DW) | | | | | |
|---|---|---|---|---|---|---|---|---|---|
| | G.a. | Caffeine | EGC | EC | EGCG | ECG | TF | TFMG | TF'MG | TfdiG |
| t = 0 | 32 | 192 | 231 | 72 | 205 | 78 | 0 | 0 | 0 | 0 |
| control t = 60 | 37 | 190 | 194 | 70 | 196 | 75 | 0 | 0 | 0 | 0 |
| tannase t = 60 | 279 | 195 | 378 | 129 | 50 | 18 | 0 | 0 | 0 | 0 |
| Net change | +246 | +3 | +147 | +57 | −155 | −60 | 0 | 0 | 0 | 0 |
| $T_{60}-t_0$ Control Fermented | 23 | 189 | 0 | 0 | 10 | 8 | 5.5 | 2 | 2 | 3 |

TABLE 6-continued

Catechin and theaflavin Composition of tannase and control teas

Mmol/g (DW)

| | G.a. | Caffeine | EGC | EC | EGCG | ECG | TF | TFMG | TF'MG | TfdiG |
|---|---|---|---|---|---|---|---|---|---|---|
| (t = 180) Tannase Fermented (t = 180) | 188 | 164 | 0 | 0 | 0 | 0 | 54 | 0 | 0 | 0 |

As one can see degallation of EGCG was only 75% complete, but there was good agreement between the reductions in EGCG and ECG and the increases in EGC and EC. Moreover there was no theaflavin formation during the tannase treatment, this indicated that under stronger vacuum provided by the pump no fermentation was taking place.

Overall there is a 10 fold increase in TF1 and a 4.3 fold increase in total TF was observed in the fermented dhool (determined by solvent extraction).

EXAMPLE 5

Process Optimisation (a) Optimisation of Tannase Dosage

Varying tannase dosage. A range of samples were prepared with increasing tannase dosage, between 5 and 320 mg tannase/kg. The results are given in Table 7 below where $L^*$, $a^*$ and $b^*$ are as before.

TABLE 7

Colour analysis of tannase/peroxide processed black teas

| Tannase | $L^*$ | $a^*$ | $b^*$ | % soluble solids |
|---|---|---|---|---|
| 5 mg/kg | 87.27 | 0.77 | 60.9 | 0.215 |
| 10 mg/kg | 86.62 | 1.42 | 62.9 | 0.205 |
| 20 mg/kg | 86.54 | 0.56 | 64.7 | 0.210 |
| 40 mg/kg | 86.3 | 1.6 | 68.1 | 0.225 |
| 80 mg/kg | 82.3 | 5.62 | 77.5 | 0.230 |
| 160 mg/kg | 81.8 | 6.4 | 82.9 | 0.245 |
| 320 mg/kg | 81.7 | 6.5 | 83.7 | 0.260 |
| Control | 90.6 | 0.37 | 42.8 | 0.185 |

These results show the teas darkened (lower L-value) and increased in colour ($a^*$ and $b^*$) with increasing tannase dosage. The inventors noted a step change in colour between using 40 and 80 mg tannase, with a 4 unit change in $a^*$ and 5 unit change in $b^*$. Soluble solids increased with tannase dosage, maximum tannase gave 40% more soluble solids than the control.

Figure 7:
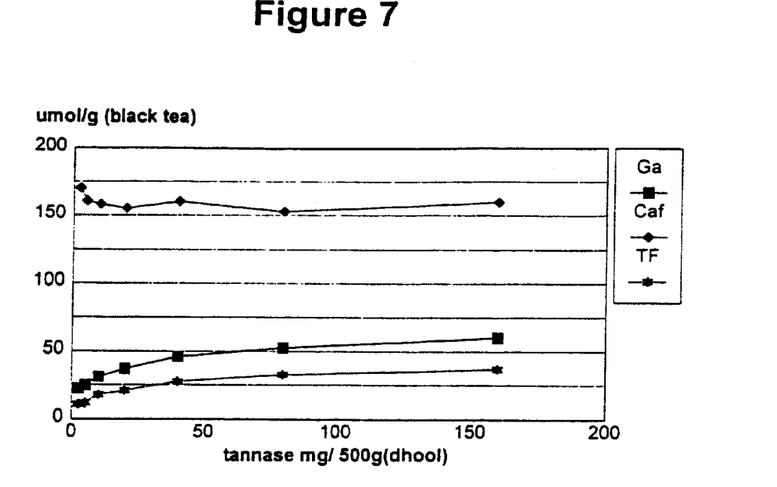
FIGS. 7 and 8 show the composition of tannase-peroxide processed black teas obtained using various tannase dosages (Example 5).
Figure 8:
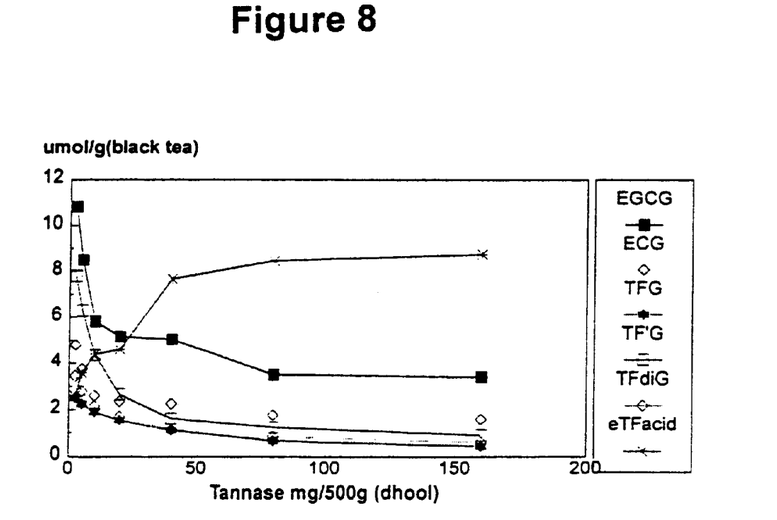
Figure 9A:
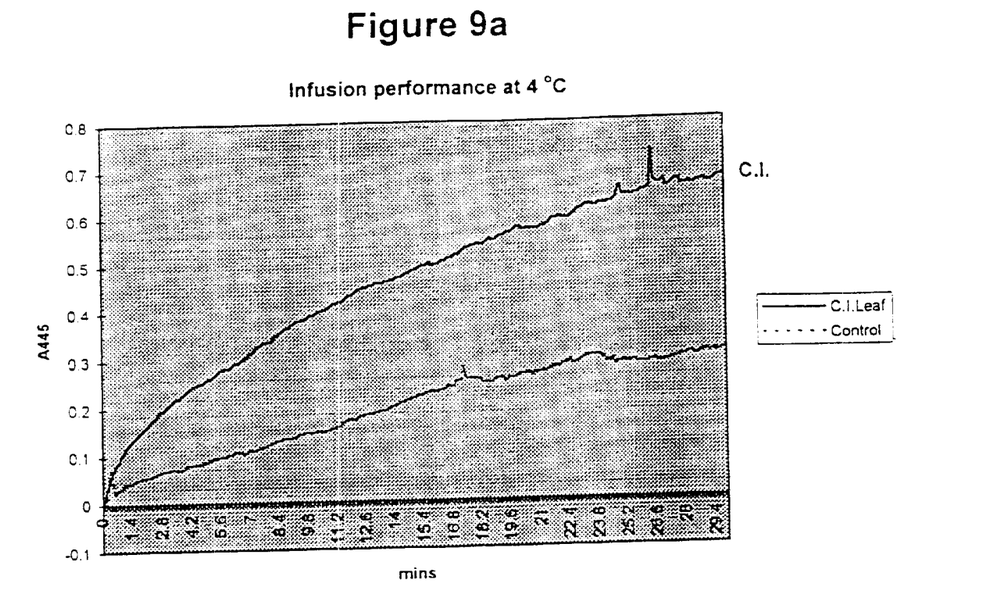
FIGS. 9a to 9e are infusion profiles of untreated and tannase-peroxide treated teas at 4° C., 15° C., 25° C., 55° C. and 70° C. respectively (Example 6).
Figure 9B:
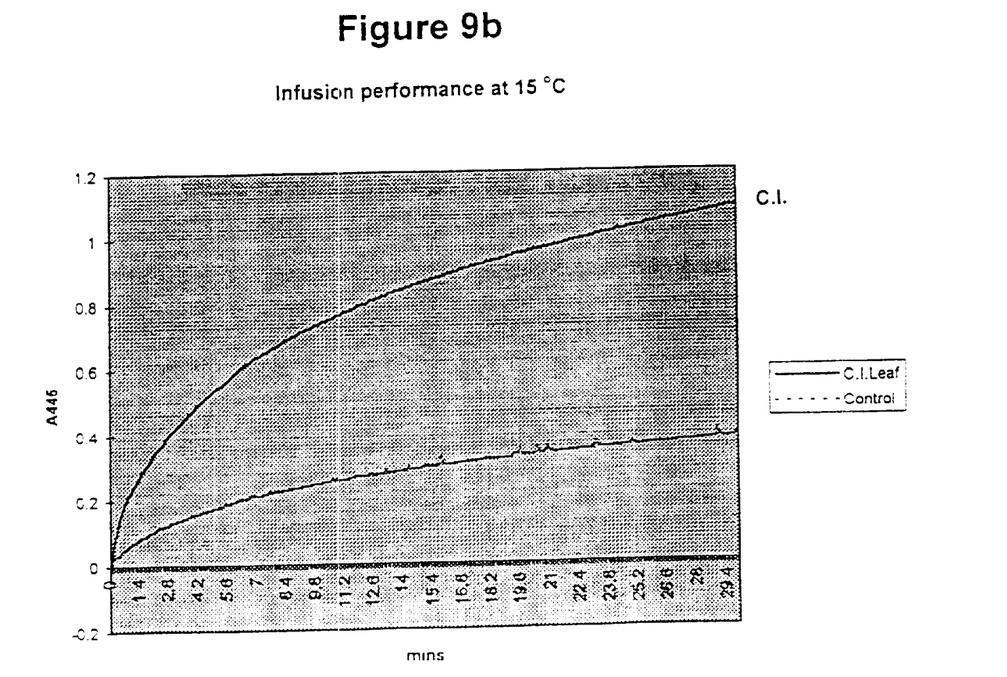
Figure 9C:
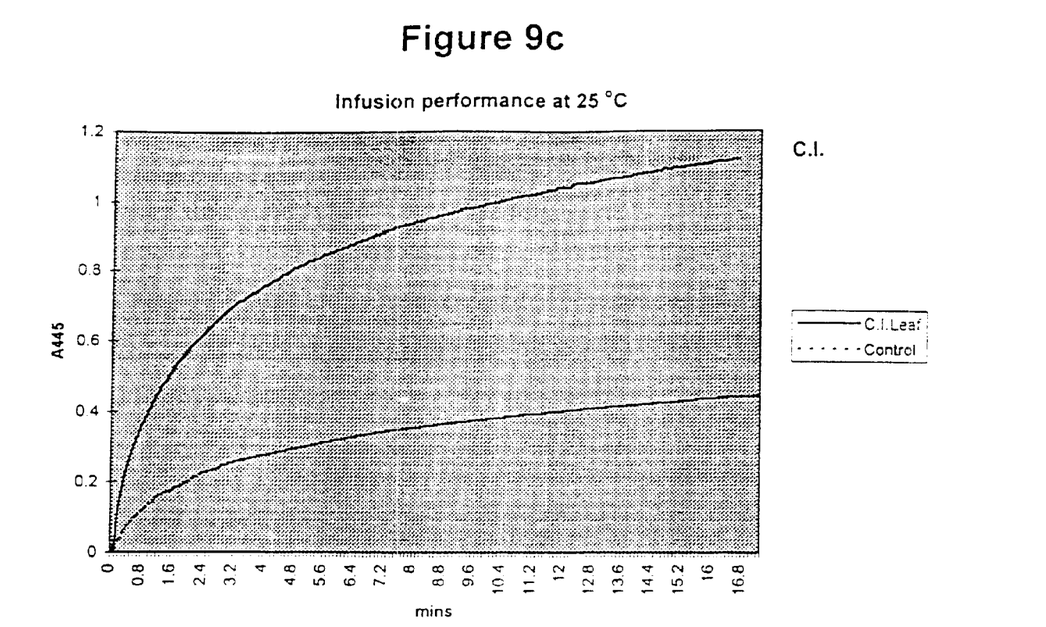
Figure 9D:
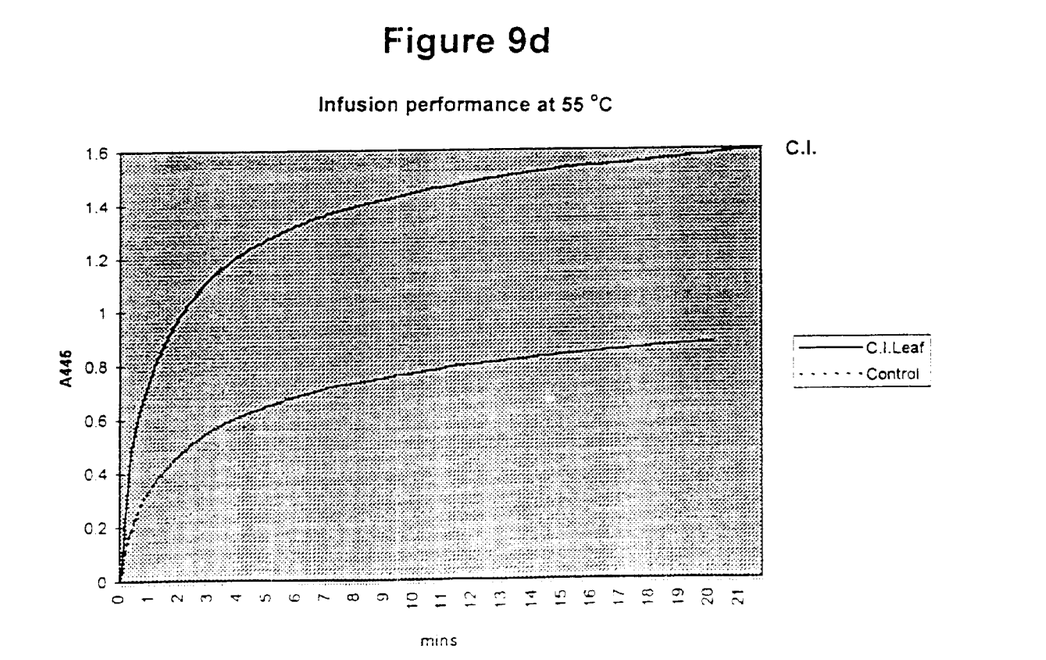
Figure 9E:
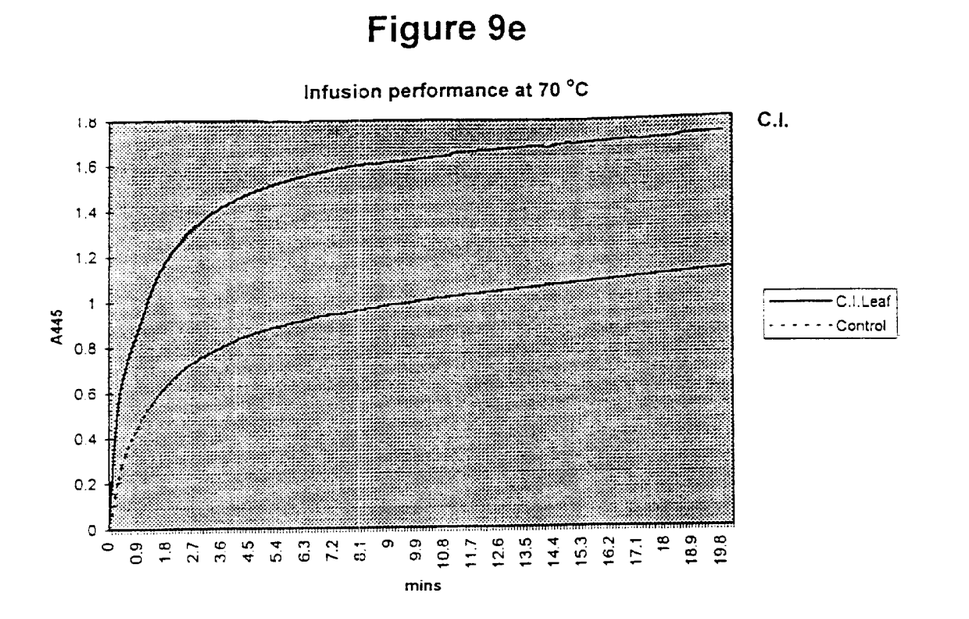

The composition of tannase-peroxide processed black teas obtained from various tannase dosage are represented in FIGS. 7 and 8.

It is clear from these results that gallic acid, theaflavin and epitheaflavic acid increase with tannase dosage, whilst residual catechins and gallated theaflavins fall.

(b) Further Enhancements

Varying Peroxide Dosing

A comparison was made between adding water and different amounts of hydrogen peroxide, as above after 60 minutes fermentation. To 1 kg of dhool 80 mg tannase was added in 100 ml water, and after 60 minutes fermentation 160 ml of water or hydrogen peroxide solution (28 to 112 ml of 30% w/w was made up to 160 ml) was added. Colour measurements were made on the products and these are shown in Table 8 below.

TABLE 8

Peroxide dosing

| Sample | $L^*$ | $a^*$ | $b^*$ | Solids |
|---|---|---|---|---|
| Water | 87.39 | 1.61 | 78.53 | 0.26 |
| HP1 | 83.08 | 6.22 | 88.38 | 0.27 |
| HP2 | 82.57 | 5.85 | 86.39 | 0.22 |
| HP3 | 81.87 | 5.79 | 80.38 | 0.22 |

HP1 - 28 ml peroxide + 132 ml water;
HP2 - 56 ml peroxide + 104 ml water;
HP3 - 112 ml peroxide + 48 ml water There was little difference in colour between the different levels of hydrogen peroxide usage, but an indication that the level of solids extracted decreased with the higher amounts used.

Varying Time of Fermentation Time After Addition of Peroxide

The length of fermentation after the addition of peroxide was varied from 0 to 60 minutes. There was little difference observed between 15 to 60 minutes, but addition and immediate firing did result in a slight reduction in infusion colour.

Effect of CTC vs No CTC After Peroxide Application

Samples were prepared under standard conditions. Colour measurements were made on the products and these are given in Table 9 below.

TABLE 9

| Sample | $L^*$ | $a^*$ | $b^*$ | Solids |
|---|---|---|---|---|
| CTC | 80.42 | 7.70 | 86.41 | 0.27 |
| No CTC | 81.65 | 7.42 | 87.81 | 0.26 |

This shows omitting the CTC after peroxide addition has a slight deleterious effect.

Effect of Water Volume During Tannase Application

Water volume was varied between 80 mg tannase in 60 to 160 ml water/kg dhool. Colour measurements were made on the products and these are given in Table 10 below.

TABLE 10

| Sample | $L^*$ | $a^*$ | $b^*$ | Solids |
|---|---|---|---|---|
| 60 ml | 83.25 | 3.90 | 81.49 | 0.24 |
| 80 ml | 82.15 | 5.64 | 83.67 | 0.24 |
| 100 ml | 81.98 | 5.68 | 85.75 | 0.25 |

TABLE 10-continued

| Sample | L* | a* | b* | Solids |
| --- | --- | --- | --- | --- |
| 120 ml | 82.00 | 8.19 | 87.57 | 0.27 |
| 140 ml | 82.21 | 5.53 | 80.97 | 0.22 |
| 160 ml | 83.59 | 3.85 | 78.74 | 0.20 |

It was interpreted from these results that the optimum level for infusion performance 100–120 ml. The lower limit 100 was chosen in order to keep added moisture to a minimum.

Effect of Increasing Fermentation Time

Fermentation time after tannase application was increased from 105 minutes (standard) to 120, 135, 150 minutes. Fermentation time after peroxide was kept at 15 minutes. The temperature was kept constant at 22° F. Colour measurements were made on the products and these are given in Table 11 below.

TABLE 11

| Sample | L* | a* | b* | Solids |
| --- | --- | --- | --- | --- |
| Std | 84.12 | 4.24 | 86.10 | 0.22 |
| 120 | 83.25 | 5.18 | 90.03 | 0.20 |
| 135 | 83.22 | 5.08 | 89.21 | 0.21 |
| 150 | 81.64 | 6.93 | 92.60 | 0.22 |

These results indicated that infusion performance increased as fermentation time increased.

Effect of Increasing Fermentation Temperature

Fermentation temperature was increased 22° C., 25° C., 30° C., 35° C., 40° C. The longest fermentation time above was used (150 minutes+15 minutes). Colour measurements were made on the products and these are shown in Table 12 below.

TABLE 12

| Sample | L* | a* | b* | Solids |
| --- | --- | --- | --- | --- |
| 22C | 81.64 | 6.93 | 92.60 | 0.22 |
| 25C | 83.52 | 5.93 | 89.24 | 0.22 |
| 30C | 81.59 | 6.33 | 80.89 | 0.22 |
| 35C | 76.54 | 9.64 | 85.13 | 0.23 |
| 40C | 79.20 | 7.09 | 82.95 | 0.22 |

It appeared from these results that performance increased as the temperature rose, up to a maximum of 30–35° C. was selected as optimum as this is the highest temperature consistently achievable during factory fermentation.

Effect of Multiple Peroxide Dosing (Extended Fermentation Time and Elevated Temperature)

Standard peroxide (56 ml peroxide+104 ml water), 15 minute ferment after addition. 2 Half peroxide (28 ml peroxide+52 ml water), 10 minutes fermentation after each addition. 2 STD peroxide (56 ml peroxide+24 ml water), 10 minutes fermentation after each addition. Colour measurements were made on the products and these are given in Table 13 below.

TABLE 13

| Sample | L* | a* | b* | Solids |
| --- | --- | --- | --- | --- |
| STD | 80.33 | 5.29 | 83.77 | 0.24 |
| 2 1/2 | 83.46 | 3.10 | 79.54 | 0.21 |
| 2 STD | 76.98 | 8.51 | 81.74 | 0.23 |

The results showed that doubling the dose of peroxide gave a benefit but splitting the standard dose into two applications seemed to reduce the infusion performance.

EXAMPLE 6

Infusion Rate Comparison

The infusion rate of 1.0 g for untreated tea and tannase-peroxide tea in 300 ml was determined by measuring the absorbance at 445 nm at various time intervals. These tests were conducted at 4° C., 15° C., 25° C., 55° C. and 70° C. respectively. The results are given in FIGS. 7a to 7e (Note C.I. in the drawings means "cold infusing" i.e. the tannase-peroxide treated tea). As one can see, the tannase-peroxide treated tea infused faster and to a greater extent at all temperatures.

EXAMPLE 7

Mature Leaf Tea Processing

Mature leaf tea, tea leaf material harvested in a 35 day cycle in portions of four leaves and a bud, was used as the raw material for the lab scale process described in Example 1. The infusion performance of the resulting cold water infusing leaf was measured as before using a MINOLTA™ calorimeter. The results are given in Table 14 below.

TABLE 14 infusion performance of product made from mature tea leaf material

| | L* | a* | B* |
| --- | --- | --- | --- |
| Run 1 | 71.4 | 13.4 | 85.5 |
| Run 2 | 72.1 | 12.1 | 84.2 |
| Run 3 | 78.2 | 5.7 | 75.7 |
| Run 4 | 75.7 | 7.9 | 73.9 |
| Run 5 | 74.2 | 6.8 | 78.4 |
| Standard Leaf | 81.8 | 3.2 | 74.5 |

When compared with the typical infusion performance of products made from standard leaf about a 10 L-unit gain in colour was seen, decreasing to 3 L-units in some cases. In all cases the taste profile of the samples made using mature tea leaf material were preferred over the control.

What is claimed is:

1. A method for preparing a cold water infusing leaf tea comprising the steps of macerating green tea leaves, treating the macerated leaves with tannase by direct application of the tannase to the macerated leaves in a solid state, fermenting the tannase-treated macerate for a time that is sufficient to generate gallic acid and theaflavin, continuing the fermentation in the presence of an amount of hydrogen peroxide that is sufficient to activate endogenous peroxidases to produce a fermented leaf material, and drying the fermented leaf material to yield the cold water infusible leaf tea.

2. A method according to claim 1, wherein the macerated leaves are tannase treated under anaerobic conditions.

3. A method according to claim 1, wherein the tannase is added in a concentration between 10 and 80 mg/kg dhool.

4. A method according to claim 3, wherein the tannase is added in a concentration between 40 and 80 mg/kg dhool.

5. A method according to claim 1, wherein the macerated tea leaves are vacuum impregnated with the tannase.

6. A method according to claim 5, wherein the tea leaves are subjected to a vacuum less than 100 mbar.

7. A method according to claim 1, wherein the fermentation is carried out for a temperature between 15 and 40° C.

8. A method according to claim 1, wherein the fermentation is carried out at a pH between 4.0 and 5.5.

9. A method according to claim 1, wherein the fermentation is carried out for a time between 30 and 150 minutes.

10. A method according to claim 1, wherein the hydrogen peroxide is added in a concentration of between 100 and 200 ml of 2.0 to 2.5% hydrogen peroxide per kg dhool.

11. A method according to claim 10, wherein the hydrogen peroxide is added in a concentration of about 160 ml of 2% peroxide per kg dhool.

12. A method according to claim 10, wherein the hydrogen peroxide is added after a time that is sufficient to generate gallic acid and theaflavin during the fermentation and thereby activate endogenous peroxidase.

13. A method for generating color species in a cold water infusing tea product comprising adding hydrogen peroxide to a macerate of green tea that, in the solid state, was treated with tannase in an amount that is sufficient for endogenous peroxidases to oxidise gallic acid liberated by tannase treatment and oxidise theaflavin produced.

* * * * *